(12) United States Patent
Hwang et al.

(10) Patent No.: US 12,339,273 B2
(45) Date of Patent: Jun. 24, 2025

(54) BLOOD ANALYSIS APPARATUS

(71) Applicant: MARK-B Inc., Seongnam-si (KR)

(72) Inventors: Hyun Doo Hwang, Seongnam-si (KR); Soo Jeong Shin, Seoul (KR); Jae Kyu Choi, Seoul (KR)

(73) Assignee: MARK-B Inc., Seongnam-si (KR)

( * ) Notice: Subject to any disclaimer, the term of this patent is extended or adjusted under 35 U.S.C. 154(b) by 1076 days.

(21) Appl. No.: 17/078,649

(22) Filed: Oct. 23, 2020

(65) Prior Publication Data

US 2021/0041415 A1    Feb. 11, 2021

Related U.S. Application Data

(63) Continuation of application No. PCT/KR2018/004820, filed on Apr. 25, 2018.

(51) Int. Cl.
*G01N 33/487* (2006.01)
*B01L 3/00* (2006.01)

(52) U.S. Cl.
CPC .. *G01N 33/48707* (2013.01); *B01L 3/502753* (2013.01); *B01L 2200/0631* (2013.01);
(Continued)

(58) Field of Classification Search
CPC ........... G01N 33/48707; G01N 33/491; G01N 33/48778; G01N 33/49; B01L 3/502753; B01L 2200/0631; B01L 2200/10; B01L 2300/0645; B01L 2400/0415; B01L 2200/026; B01L 2200/0605; B01L 2300/0681; B01L 2300/161; B01L 2400/0406; B01L 2400/0427; B01L 3/502; B01L 3/502761; B01L 2200/0652;
(Continued)

(56) References Cited

U.S. PATENT DOCUMENTS 6,194,224 B1 * 2/2001 Good ............... G01N 33/54388
436/805
2004/0126814 A1 * 7/2004 Singh ....................... C08F 8/00
435/7.1
(Continued)

FOREIGN PATENT DOCUMENTS

JP        4184074 B2    11/2008
KR   10-1046156 B1     7/2011

OTHER PUBLICATIONS

International Search Report issued in PCT/KR2018/004820; mailed Apr. 3, 2019.

*Primary Examiner* — Jill A Warden
*Assistant Examiner* — Jacqueline Brazin
(74) *Attorney, Agent, or Firm* — Studebaker Brackett PLLC

(57) ABSTRACT

The present invention relates to a blood analysis device including: a membrane configured to separate plasma from blood, a channel into which the plasma separated by the membrane is introduced, an electrode part including electrodes configured to adjoin one surface of the channel and come into contact with the plasma flowing in the channel, and a channel cover configured to adjoin a surface opposite to one surface of the channel which is adjoined by the electrode part, in which when any one of the electrode part and the channel cover adjoins the membrane, a part of the membrane covers an upper portion of the electrode part or the channel cover.

19 Claims, 15 Drawing Sheets

(52) U.S. Cl.
CPC ... *B01L 2200/10* (2013.01); *B01L 2300/0645* (2013.01); *B01L 2400/0415* (2013.01)

(58) Field of Classification Search
CPC ....... B01L 2300/041; B01L 2300/0848; B01L 2300/0861
USPC ...................................................... 435/287.2
See application file for complete search history.

(56) References Cited

U.S. PATENT DOCUMENTS

| | | | |
|---|---|---|---|
| 2005/0158704 A1* | 7/2005 | Tyvoll | A61B 5/14532 435/4 |
| 2010/0187105 A1* | 7/2010 | Unger | F16K 99/0015 156/60 |
| 2016/0153935 A1* | 6/2016 | Nishigaki | G01N 15/1459 204/601 |
| 2018/0093269 A1* | 4/2018 | Rachamim | B01L 3/502738 |

* cited by examiner

[FIG. 1]
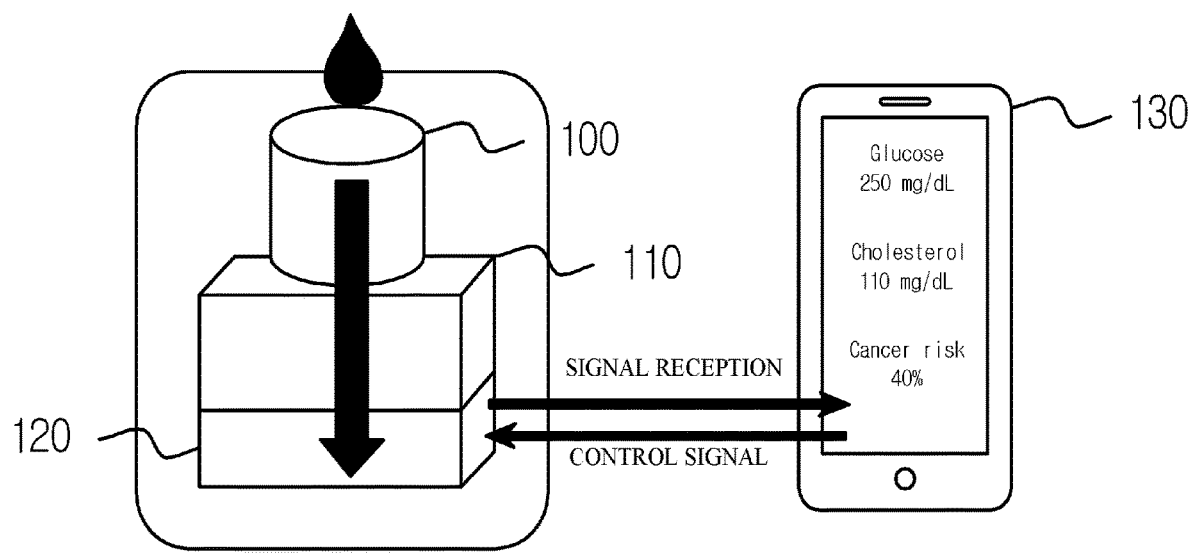

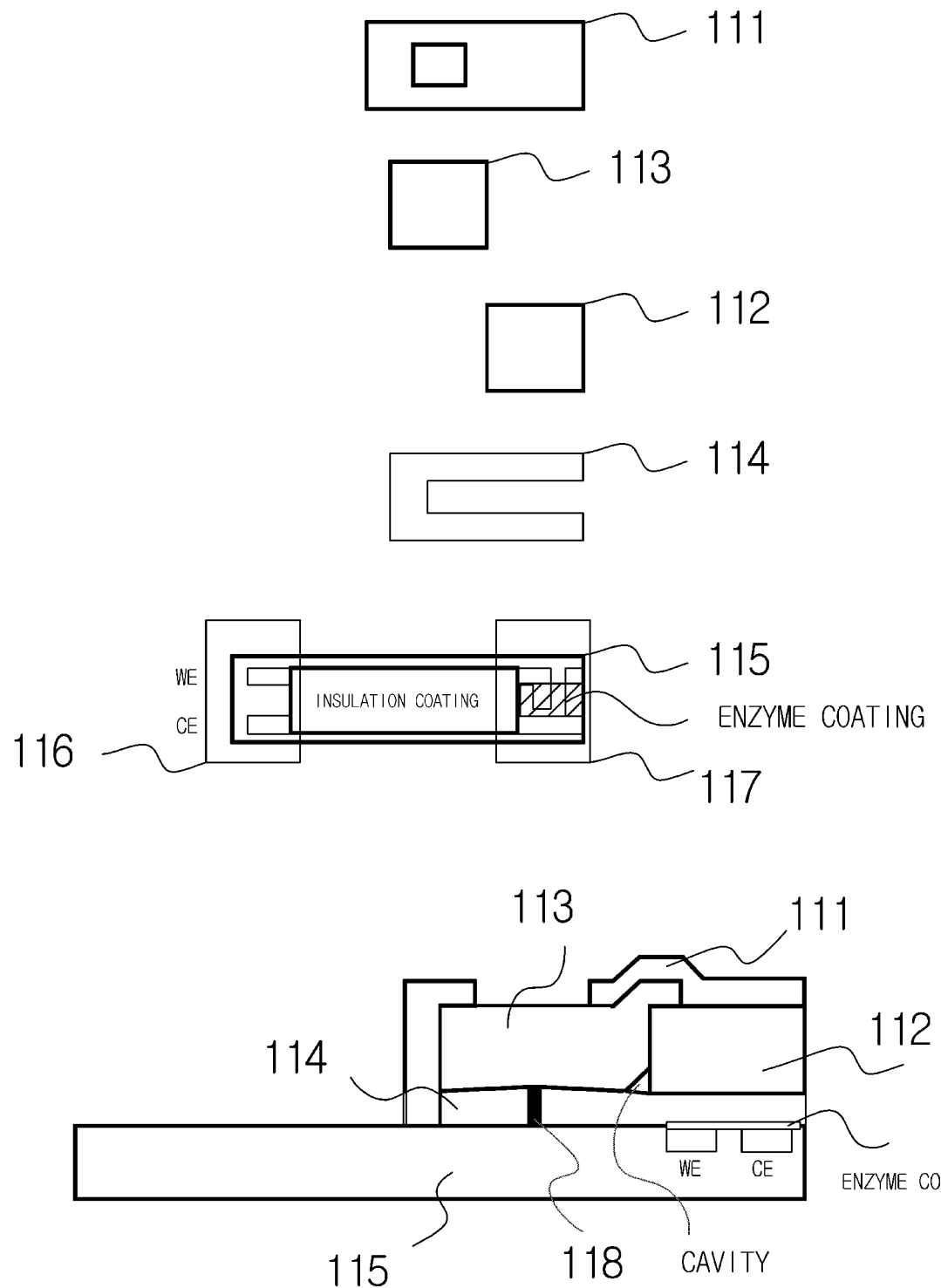

[FIG. 3]
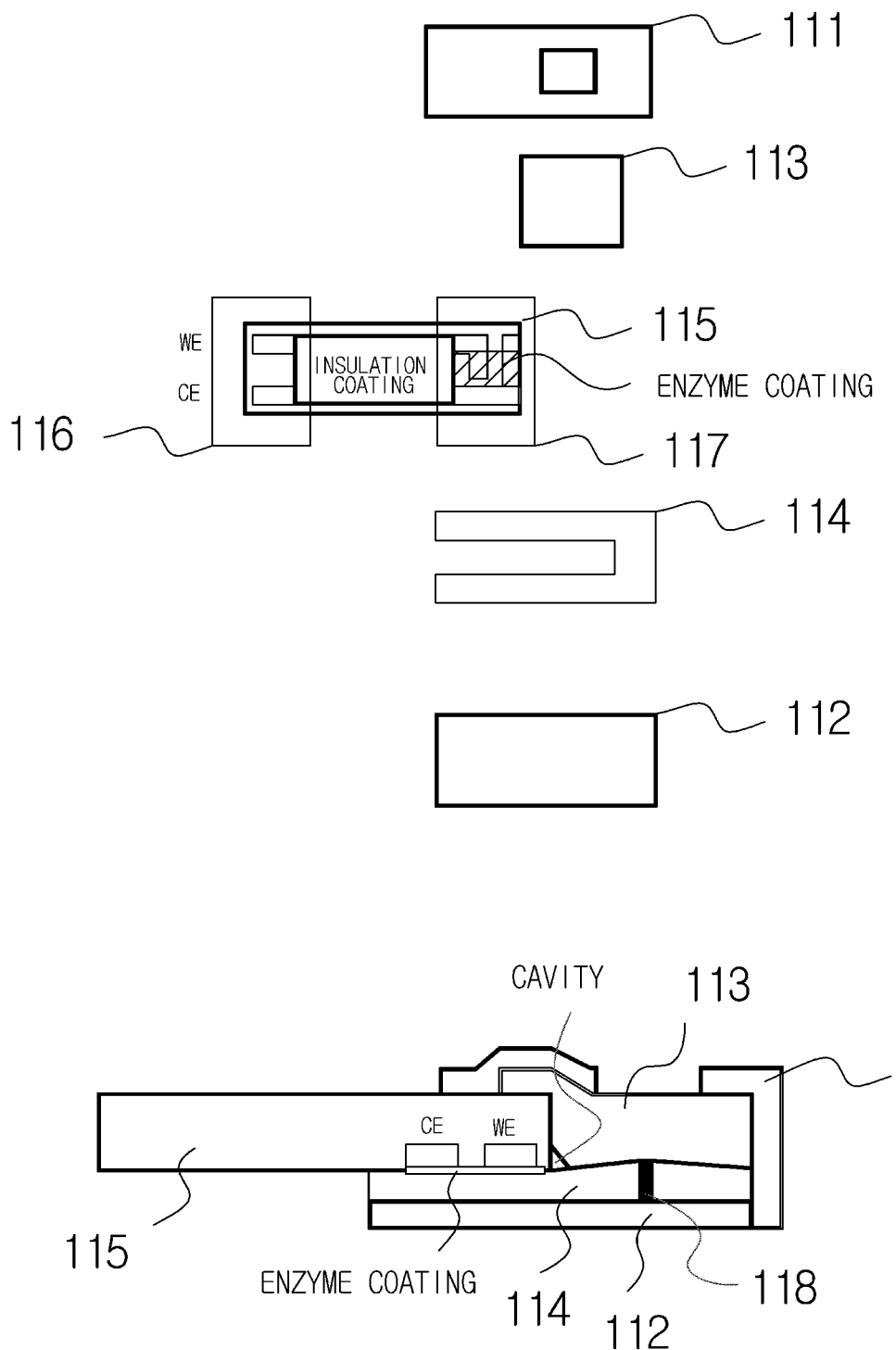

[FIG. 4]
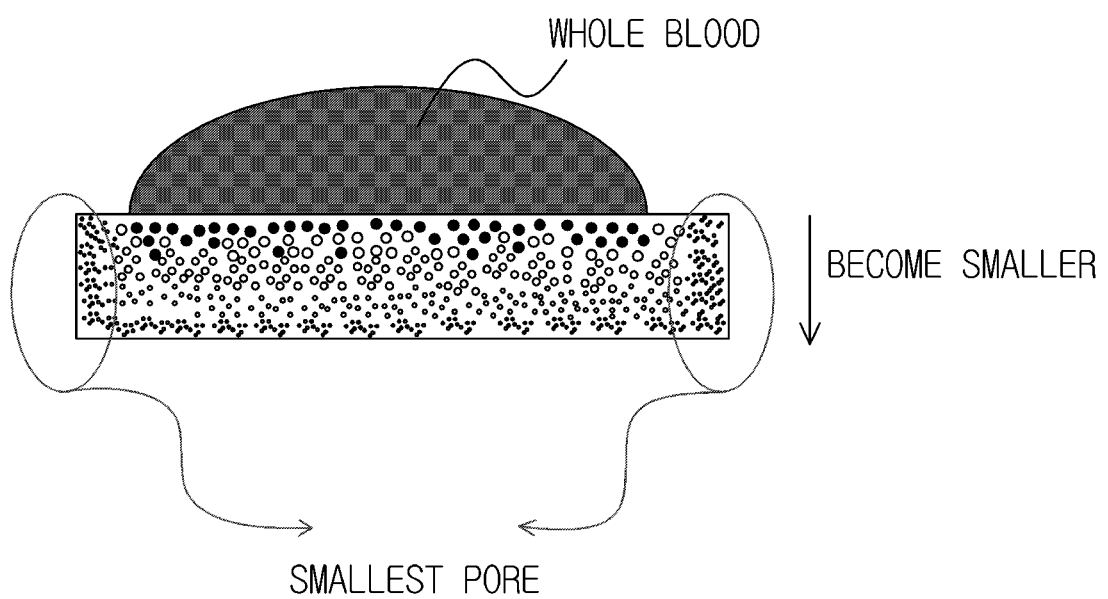

[FIG. 5A]
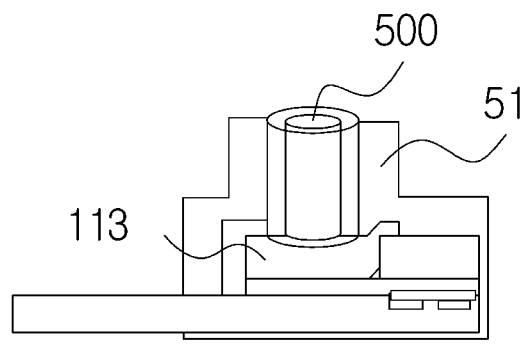
[FIG. 5B]
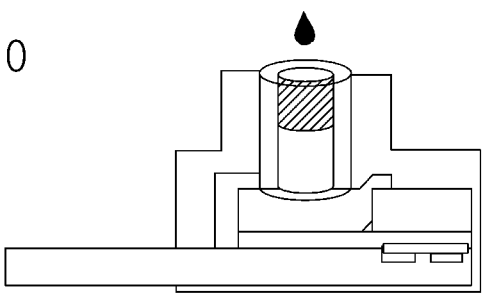
[FIG. 5C]
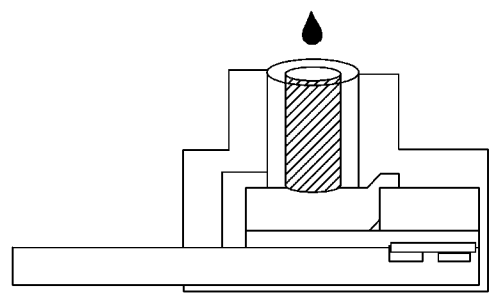
[FIG. 5D]
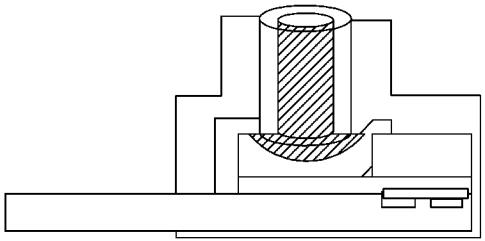
[FIG. 5E]
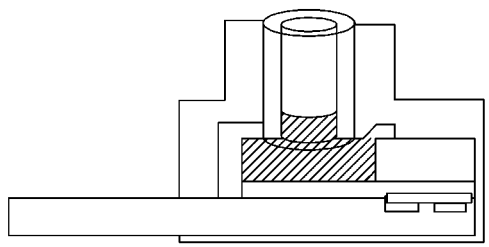

[FIG. 6A]
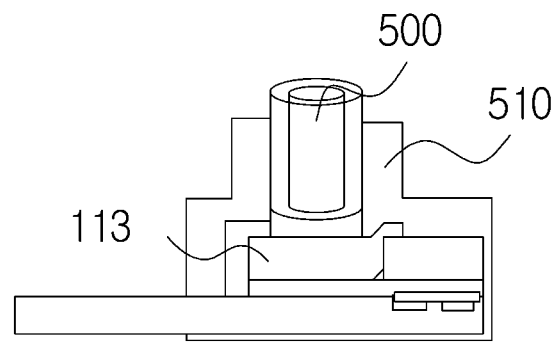
[FIG. 6B]
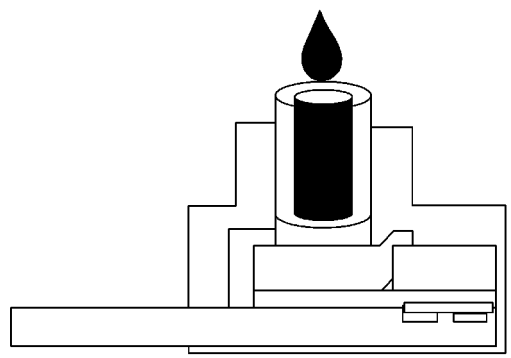
[FIG. 6C]
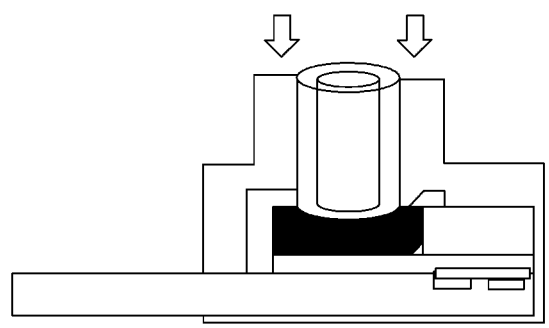

[FIG. 7A]
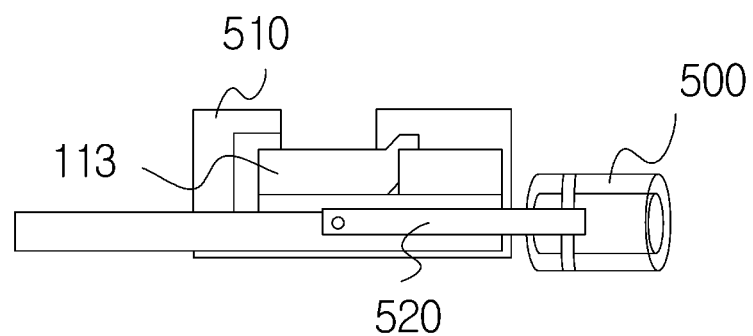
[FIG. 7B]
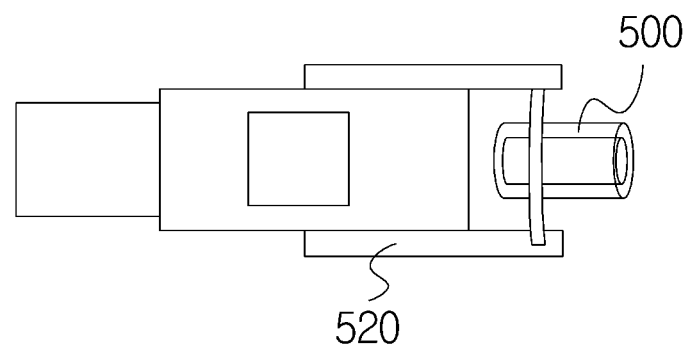

[FIG. 8A]
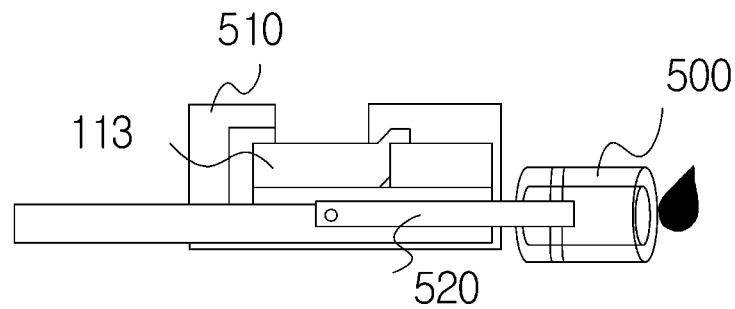
[FIG. 8B]
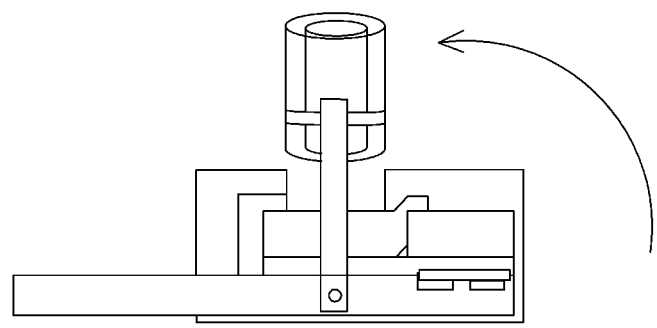
[FIG. 8C]
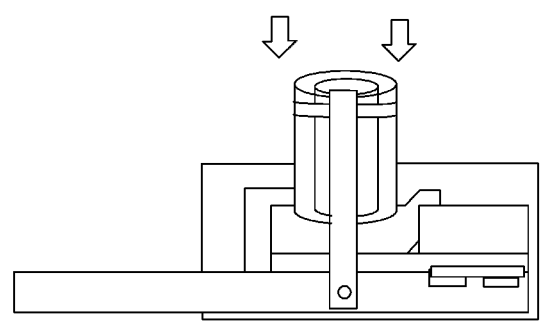

[FIG. 9A]
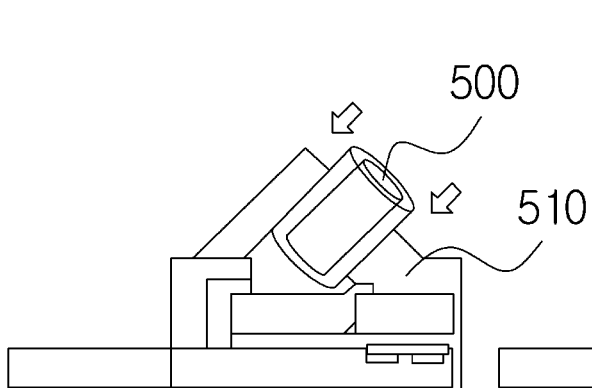
[FIG. 9B]
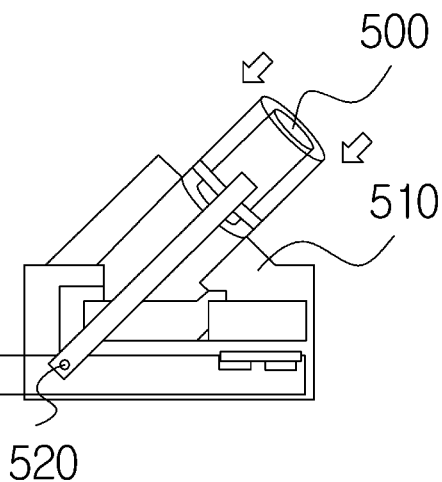
[FIG. 9C]
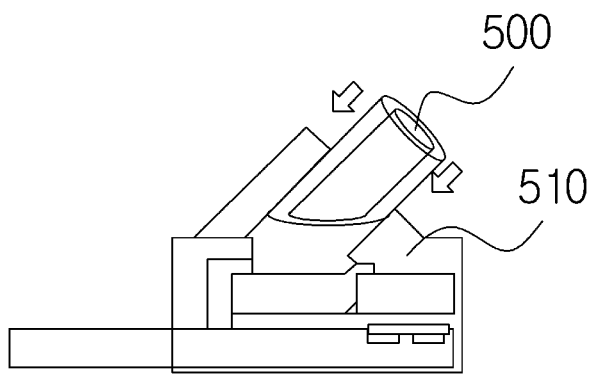
[FIG. 10A]
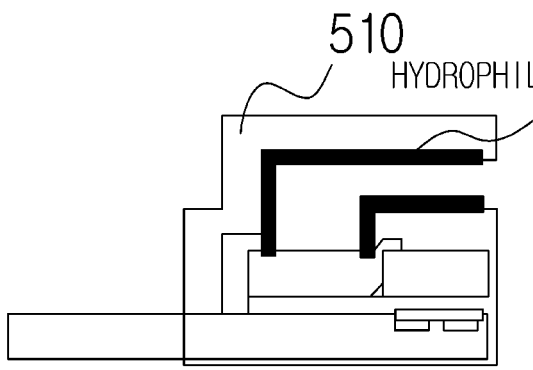
[FIG. 10B]
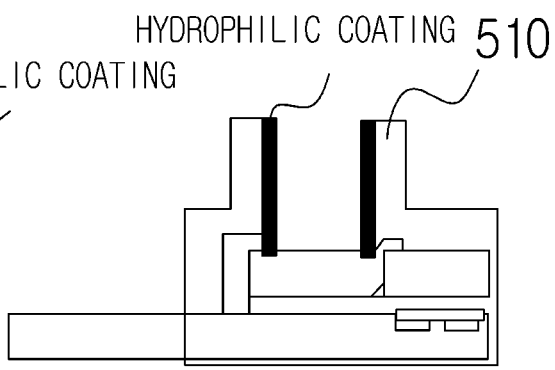

[FIG. 11A]
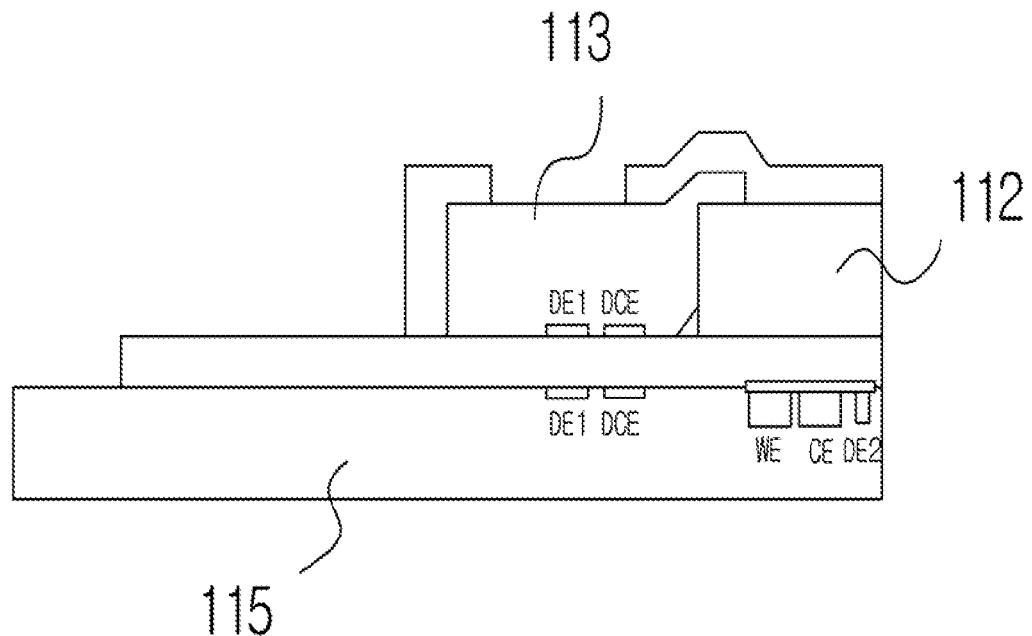
[FIG. 11B]
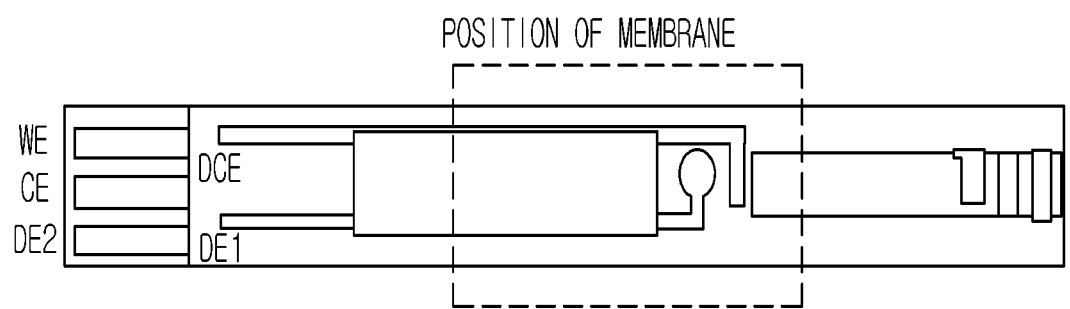

[FIG. 11C]
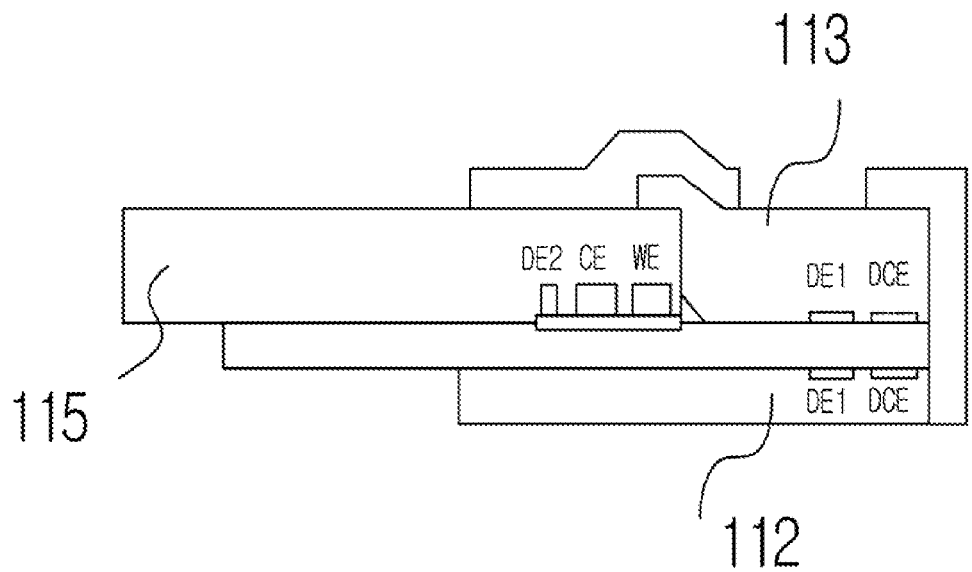
[FIG. 11D]
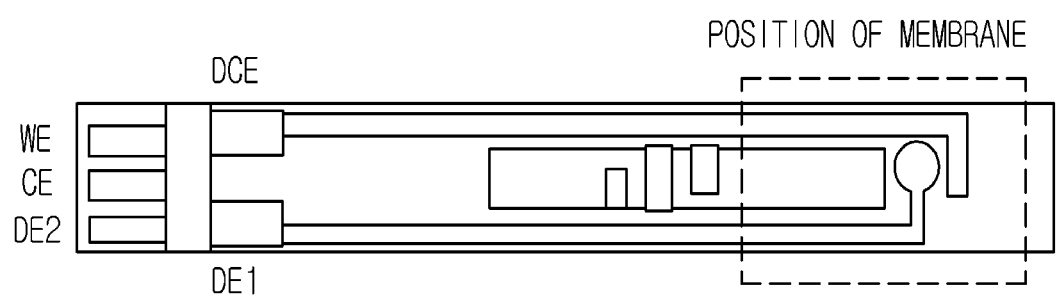

[FIG. 12A]
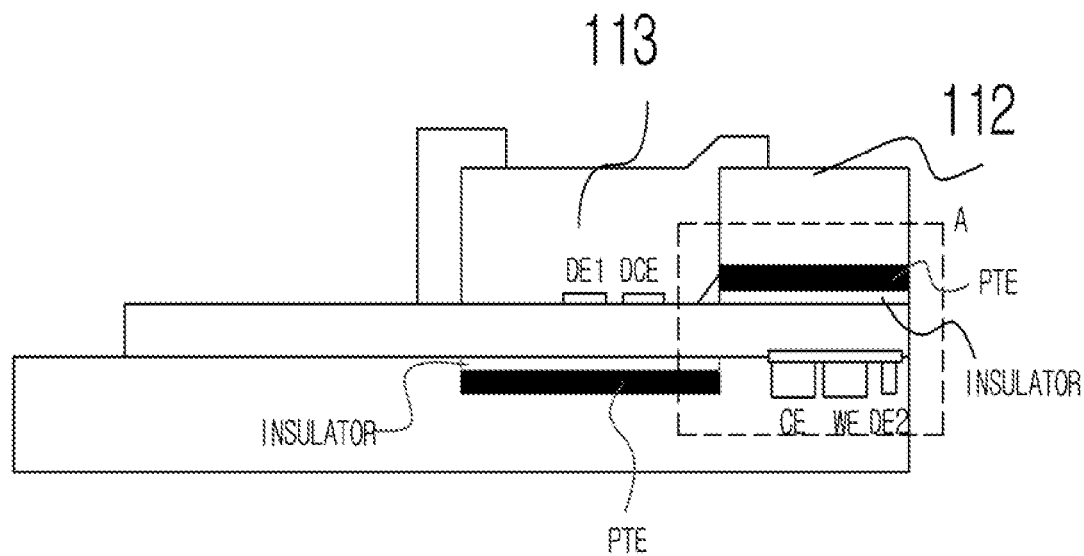
[FIG. 12B]
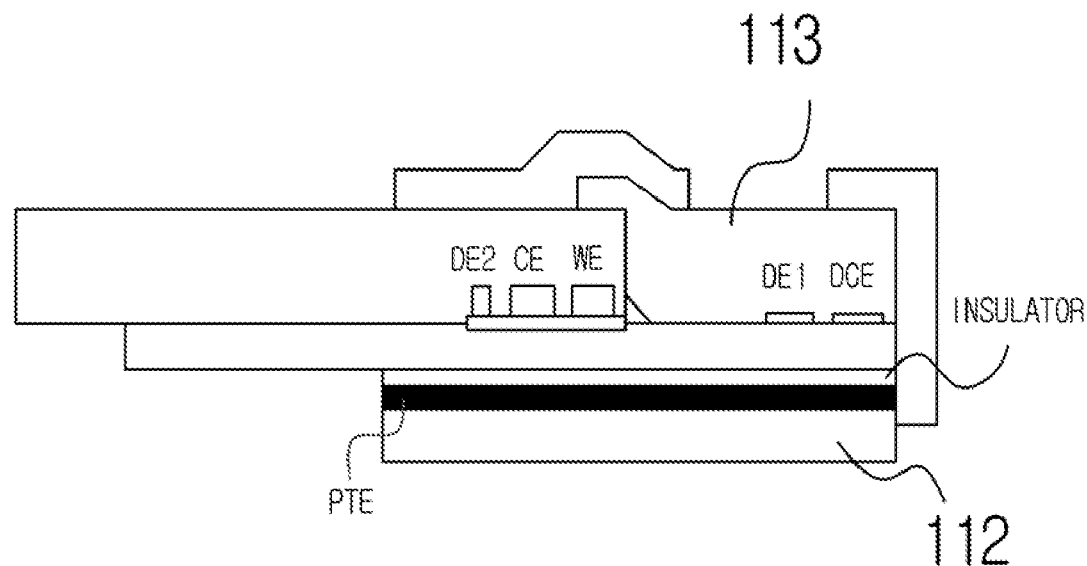

[FIG. 13]
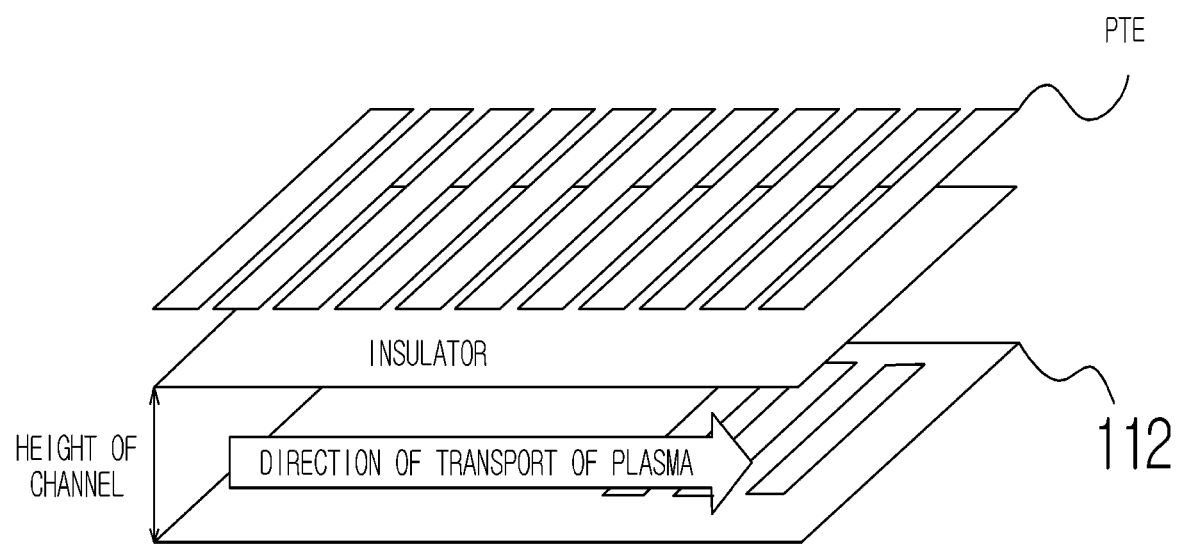

[FIG. 14A]
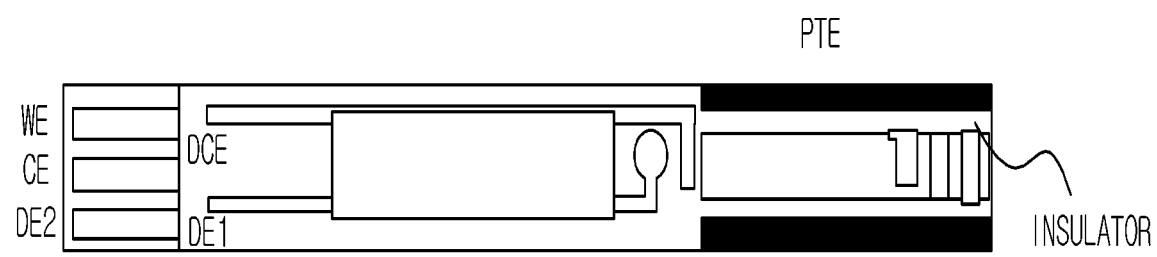
[FIG. 14B]
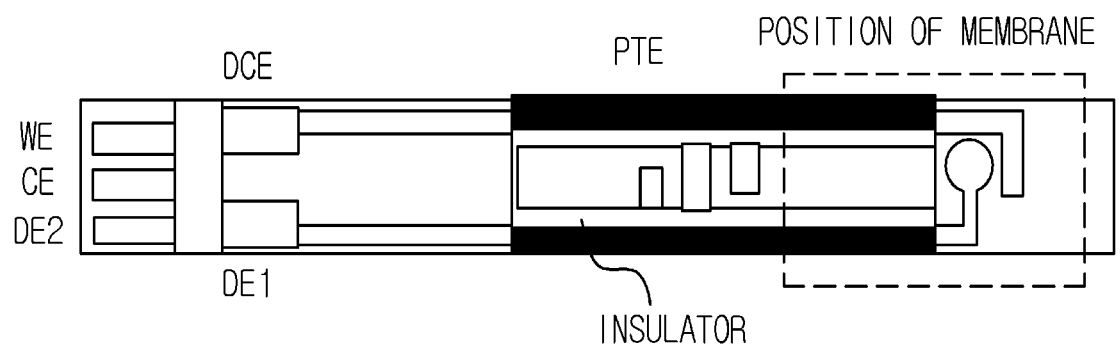

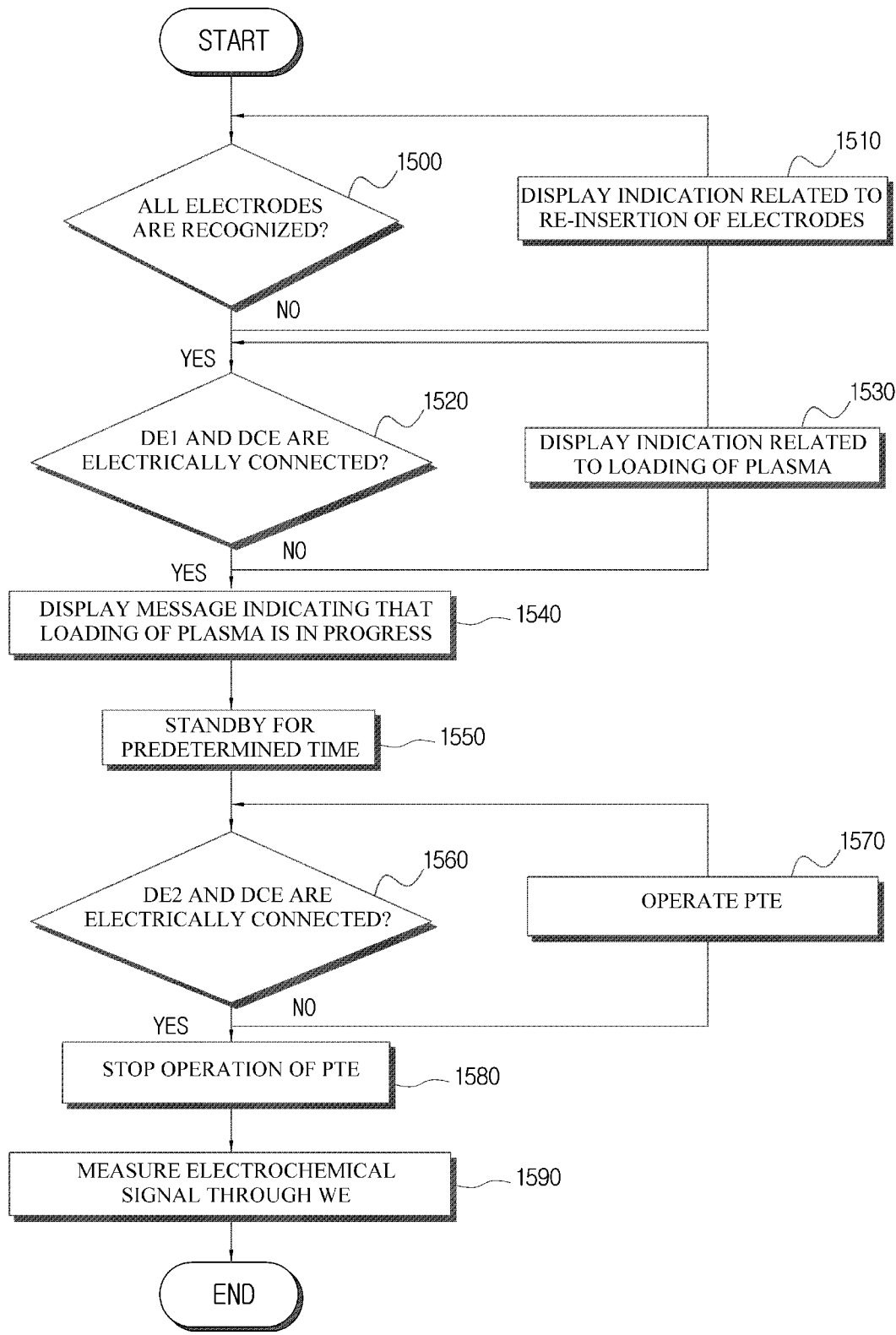
[FIG. 15]

BLOOD ANALYSIS APPARATUS

CROSS-REFERENCE TO RELATED APPLICATIONS

The present application is a continuation of International Patent Application No. PCT/KR2018/004820, filed on Apr. 25, 2018. The disclosure of the above application is hereby incorporated by reference herein in its entirety.

TECHNICAL FIELD

The present invention relates to a blood analysis device, and more particularly, to a blood analysis device, in which a part of a membrane covers an upper portion of a channel cover or an electrode part, such that plasma passing through the membrane is prevented from flowing into a space between the membrane and the electrode part or between the membrane and the channel cover.

BACKGROUND ART

A lab-on-a-chip technology is a kind of technology for manufacturing biochips. A nano-passageway is made by using a material such as plastic, glass, or silicon, and an infinitesimal amount of sample flows into the passageway, thereby enabling an experiment to be quickly performed. The amount of one drop of blood is 3 to 4 cc, and the number of white blood cells in a cancer patient may be measured from the amount equivalent to one three-millionth the amount of one drop of blood.

Items, which may be diagnosed from blood, include blood glucose, anemia, cholesterol, myocardial infarction, liver functions, cancer, and the like.

The blood glucose refers to the amount of glucose contained in the blood. The blood glucose is used as an important test measure because of the recent increase in diabetic patients. In addition, anemia may be diagnosed by checking the number of red blood cells, hemoglobin, and hematocrit.

Cardiac muscle contains various types of enzymes such as AST, CPK, and LDH, and also includes protein such as Troponin-I and Troponin-T. In case of necrosis of the cardiac muscle caused by myocardial infarction, these enzymes and proteins flow out and into the blood, and the amount of enzymes and proteins flowing into the blood is also increased as a range of the necrosis is increased. Among them, in the event of acute myocardial infarction, the amount of CK-MB is increased first in the blood, the amount of AST is increased sequentially, and then the amount of LDH is increased lastly. The enzymes such as AST, CPK, and LDH exist not only in the cardiac muscle, but also in other organs, and as a result, in the case of an increase in amount of enzymes, it cannot be said that the increase in amount of enzymes necessarily results from the myocardial infarction. However, if the increase in amount of enzymes is accompanied by chest pain, it can be assumed that the increase in amount of enzymes is caused by myocardial infarction. Troponin-I and troponin-T are proteins that are not present in other organs, and as a result, if these proteins are found in the blood, it means that the cardiac muscle is damaged. Therefore, the analysis of Troponin-I and troponin-T is helpful in the diagnosis of myocardial infarction.

Meanwhile, a method of diagnosing cancer by analyzing proteins present in blood has been introduced. As an example, there is a cancer diagnosis method using ribosomal protein S3 (rpS3) expressed in cancer cells and secreted out of the cancer cells. As another example, there has been introduced a method of diagnosing cancer by obtaining peptides through a hydrolysis process using enzymes from glycoproteins related to cancer development, selecting specific peptides related to glycosylation showing specific quantitative changes in accordance with cancer development, and then using, as markers, the selected specific peptides related to glycosylation.

On the other hand, in the situation in which the biochip is being developed for diagnosing, from blood, blood glucose, anemia, cholesterol, myocardial infarction, liver functions, cancer, and the like, there is a need for a method capable of improving sensitivity of a diagnosis chip by maximizing an antigen/antibody reaction by increasing a recovery rate of plasma components made by separating blood cell components from blood by using a membrane of the biochip.

Document 1 (KR 10-1046156 B1) discloses that each edge of a membrane is prevented as much as possible from coming into contact with a structure made by joining an upper substrate and a lower substrate, thereby preventing loaded blood from leaking in an undesired direction. However, there is a need for a further simplified structure to effectively prevent a leakage of blood.

DISCLOSURE

Technical Problem

Therefore, a first object to be achieved by the present invention is to provide a blood analysis device, in which a part of a membrane covers an upper portion of a channel cover or an electrode part, such that plasma passing through the membrane is prevented from flowing into a space between the membrane and the electrode part or between the membrane and the channel cover.

A second object to be achieved by the present invention is to provide a blood analysis device capable of detecting a position of plasma flowing in a channel via a membrane.

Technical Solution

In order to achieve the first object, the present invention provides a blood analysis device including: a membrane configured to separate plasma from blood; a channel into which the plasma separated by the membrane is introduced; an electrode part including electrodes configured to adjoin a lower portion of the channel and come into contact with the plasma flowing in the channel; and a channel cover configured to cover a part of an upper portion of the channel, in which a part of the membrane covers a part of the channel cover.

According to the exemplary embodiment of the present invention, a cavity may be formed in a lower portion of a surface of the membrane with which the channel cover comes into contact.

In addition, the membrane may have pores having non-uniform sizes, and a surface of the membrane, which is adjacent to the channel cover, may have no pore or smallest pores in the membrane.

According to another exemplary embodiment of the present invention, the blood analysis device may further include a filler configured to connect the membrane and a lower surface of the channel, in which the filler pushes up, by a predetermined height, a portion of the membrane with which the filler comes into contact.

In addition, a first detecting electrode with which the plasma comes into contact may be disposed on an upper portion or a lower portion of a contact surface between the membrane and the channel.

According to still another exemplary embodiment of the present invention, the blood analysis device may further include a plasma transporting electrode and an insulator between the channel cover and the channel, in which when the plasma does not reach a second detecting electrode when a predetermined time has elapsed after the plasma comes into contact with the first detecting electrode, a polarity of the plasma transporting electrode is changed to move the plasma in the channel.

The blood analysis device may further include a plasma transporting electrode on an upper portion or a lower portion of a contact surface between the channel and the electrode part, in which when the plasma does not reach a second detecting electrode within a predetermined time after the plasma comes into contact with the first detecting electrode, a polarity of the plasma transporting electrode is changed to move the plasma in the channel.

According to yet another exemplary embodiment of the present invention, the blood analysis device may further include a plasma transporting electrode on a left or right surface of the channel, in which a polarity of the plasma transporting electrode is changed to move the plasma in the channel.

In order to achieve the second object, the present invention provides a blood analysis device including: a membrane configured to separate plasma from blood; a channel into which the plasma separated by the membrane is introduced; an electrode part including electrodes configured to adjoin a part of an upper portion of the channel and come into contact with the plasma flowing in the channel; and a channel cover configured to cover a lower portion of the channel, in which a part of the membrane covers a part of an upper portion of the electrode part.

According to the exemplary embodiment of the present invention, a cavity may be formed in a lower portion of a surface of the membrane with which the electrode part comes into contact.

In addition, the membrane may have pores having non-uniform sizes, and a surface of the membrane, which is adjacent to the electrode part, may have no pore or smallest pores in the membrane.

According to another exemplary embodiment of the present invention, the blood analysis device may further include a filler configured to connect the membrane and a lower surface of the channel, in which the filler pushes up, by a predetermined height, a portion of the membrane with which the filler comes into contact.

In addition, a first detecting electrode with which the plasma comes into contact may be disposed on an upper portion or a lower portion of a contact surface between the membrane and the channel.

According to still another exemplary embodiment of the present invention, the blood analysis device may further include a plasma transporting electrode and an insulator between the channel and the channel cover, in which when the plasma does not reach a second detecting electrode after a predetermined time has elapsed after the plasma comes into contact with the first detecting electrode, a polarity of the plasma transporting electrode is changed to move the plasma in the channel.

In addition, the blood analysis device may further include a plasma transporting electrode on a left or right surface of the channel, in which a polarity of the plasma transporting electrode is changed to move the plasma in the channel.

Advantageous Effects

According to the present invention, a part of the membrane covers the upper portion of the channel cover or the electrode part, such that the plasma passing through the membrane may be prevented from flowing into the space between the membrane and the electrode part or between the membrane and the channel cover.

In addition, according to the present invention, it is possible to detect the position of the plasma flowing in the channel via the membrane. Furthermore, according to the present invention, it is possible to actively move the plasma, which flows in the channel, in the direction of the detecting electrode by using the plasma transporting electrode.

DESCRIPTION OF DRAWINGS

FIG. 1 is a configuration view of a blood analysis device according to an exemplary embodiment of the present invention.

FIG. 2 is a view illustrating detailed configurations of a plasma separation part 110 and a plasma guide part 120 according to the exemplary embodiment of the present invention.

FIG. 3 is a view illustrating detailed configurations of a plasma separation part 110 and a plasma guide part 120 according to another exemplary embodiment of the present invention.

FIG. 4 is an enlarged view of a membrane 113 according to the exemplary embodiment of the present invention.

FIGS. 5A to 5E are views illustrating a detailed configuration of a stationary blood loading part 100 according to the exemplary embodiment of the present invention.

FIGS. 6A to 6C are views illustrating a detailed configuration of a stationary blood loading part 100 according to another exemplary embodiment of the present invention.

FIGS. 7A and 7B are views illustrating a detailed configuration of a rotary blood loading part 100 according to still another exemplary embodiment of the present invention.

FIGS. 8A to 8C are views illustrating a process of supplying blood to the membrane 113 by using the rotary blood loading part 100 illustrated in FIGS. 7A and 7B.

FIGS. 9A to 9C are views illustrating a state in which a capillary holder 510 is inclined at 45 degrees with respect to an upper surface of the membrane 113.

FIGS. 10A and 10B are views illustrating the blood loading part 100 in which an inner portion of the capillary holder 510 is coated with a hydrophilic coating without a capillary part 500 to load blood.

FIGS. 11A to 11D are views illustrating detecting electrodes DE1, DCE, WE, CE, and DE2 included in the plasma guide part 120 according to the exemplary embodiment of the present invention.

FIGS. 12A and 12B are views illustrating a state in which a plasma transporting electrode PTE included in the plasma guide part 120 according to the exemplary embodiment of the present invention is added to the configuration illustrated in FIGS. 11A to 11D.

FIG. 13 is an enlarged view of part A of the PTE illustrated in FIG. 12A.

FIGS. 14A and 14B are views illustrating a state in which a plasma transporting electrode PTE included in a plasma guide part 120 according to another exemplary embodiment of the present invention is added to the configuration illustrated FIGS. 11A to 11D.

FIG. 15 is a flowchart of a blood analysis method to an exemplary embodiment of the present invention.

BEST MODE

In order to achieve the first object, the present invention provides a blood analysis device including: a membrane configured to separate plasma from blood; a channel into which the plasma separated by the membrane is introduced; an electrode part including electrodes configured to adjoin a lower portion of the channel and come into contact with the plasma flowing in the channel; and a channel cover configured to cover a part of an upper portion of the channel, in which a part of the membrane covers a part of the channel cover.

MODE FOR INVENTION

Hereinafter, exemplary embodiments of the present invention will be described in detail with reference to the accompanying drawings so that those with ordinary skill in the art to which the present invention pertains may easily carry out the present invention. However, it will be apparent to those skilled in the art that the exemplary embodiments are provided for more specifically explaining the present invention and the present invention is not limited to the exemplary embodiments.

The configuration of the invention for clearly explaining the solution to the problem to be solved by the present invention will be described in detail with reference to the accompanying drawings based on the exemplary embodiment of the present invention. In giving reference numerals to constituent elements of the respective drawings, the same constituent elements will be designated by the same reference numerals even though the constituent elements are illustrated in different drawings. It should be noted in advance that constituent elements in other drawings may be cited to explain the drawings, as necessary. In addition, in the detailed description of operational principles in the exemplary embodiments of the present invention, the specific descriptions of well-known functions or configurations related to the present invention or various contents will be omitted when it is determined that the specific descriptions may unnecessarily obscure the subject matter of the present invention.

In addition, throughout this specification and the claims, when one constituent element is referred to as being "connected to" another constituent element, one constituent element can be "directly connected to" the other constituent element, and one constituent element can also be "indirectly connected to" the other element with other elements therebetween. Unless particularly stated otherwise in the present specification, a singular form also includes a plural form. The terms such as "comprises (includes)" and/or "comprising (including)" used in the specification do not exclude presence or addition of one or more other constituent elements, steps, operations, and/or elements, in addition to the mentioned constituent elements, steps, operations, and/or elements.

Terms "first", "second", and the like may be used to describe various elements, components, and/or sections, but the elements, components, and/or sections are of course not limited by these terms. These terms are merely used to distinguish one element, component, or section from other elements, components, or sections. Therefore, the first element, the first constituent element, or the first section mentioned hereinafter may of course be the second element, the second constituent element, or the second section within the technical spirit of the present invention.

When an element or layer is referred to as being "on" another element or layer, it can be directly on the other element or layer or intervening elements or layers may be present. In contrast, when an element is referred to as being "directly on" another element or layer, there are no intervening elements or layers present. Spatially relative terms, such as "below," "beneath," "lower," "above," "upper," and the like, may be used herein for ease of description of a correlation between one element or component and other elements or components, as illustrated in the drawings. It should be understood that the spatially relative terms encompass different orientations of the elements in use or operation in addition to the orientation depicted in the drawings. For example, if the element in the drawings is turned over, the element described as being "below" or "beneath" the other element may be placed "above" the other element. Thus, the exemplary term "below" can encompass both orientations of above and below. The elements may be oriented in different directions, and the spatially relative terms used herein may be interpreted in accordance with the orientations.

The terms used in the present specification are for explaining the exemplary embodiments, not for limiting the present invention. Unless particularly stated otherwise in the present specification, a singular form also includes a plural form. The term "comprise" and/or "comprising" used in the specification does not exclude existence or addition of one or more other constituent elements in addition to the mentioned constituent element. Throughout the specification, the same reference numerals denote the same constituent elements.

Unless otherwise defined, all terms (including technical and scientific terms) used in the present specification may be used as the meaning which may be commonly understood by the person with ordinary skill in the art, to which the present invention belongs. In addition, terms defined in a generally used dictionary shall not be construed in ideal or excessively formal meanings unless they are clearly and specially defined in the present specification.

FIG. 1 is a configuration view of a blood analysis device according to an exemplary embodiment of the present invention.

Referring to FIG. 1, a blood analysis device according to the present exemplary embodiment includes a blood loading part 100, a plasma separation part 110, a plasma guide part 120, and a signal analysis part 130.

The blood loading part 100 receives blood and supplies the blood to a membrane of the plasma separation part 100. The blood loading part 100 may be configured to load an accurate amount of blood into the plasma separation part 110.

The plasma separation part 110 filters out blood cells from the blood supplied from the blood loading part 100 and allows the plasma to pass therethrough. No separate power may be used to separate the plasma from the blood.

Because characteristics (e.g., viscosity) of the plasma introduced into the channel are different from sample to sample, the plasma guide part 120 guides the plasma so that the plasma flows in the channel and comes into contact with the electrode within a predetermined time. To this end, according to the exemplary embodiment of the present invention, a plasma guide electrode is provided to actively move the plasma in the channel.

The signal analysis part 130 measures and analyzes an electrical signal generated when the plasma comes into contact with the electrode, and the signal analysis part 130 displays an analysis result. The analysis result made by the signal analysis part 130 from the signal may include a glucose content, a cholesterol content, a cancer risk, and the like. In addition, the signal analysis part 130 may generate a signal for controlling an operation of the blood loading part 100, the plasma separation part 110, or the plasma guide part 120, and transmit the signal to the blood loading part 100, the plasma separation part 110, or the plasma guide part 120.

FIG. 2 is a view illustrating detailed configurations of a plasma separation part 110 and a plasma guide part 120 according to an exemplary embodiment of the present invention, and FIG. 3 is a view illustrating detailed configurations of a plasma separation part 110 and a plasma guide part 120 according to another exemplary embodiment of the present invention.

Referring to FIGS. 2 and 3, the plasma separation part 110 according to the present exemplary embodiment includes a loading hole cover 111, a channel cover 112, and a membrane 113, and the plasma guide part 120 includes a channel 114, an electrode part 115, and a filler 118. The electrode part 115 includes a device recognition unit 116 and a reaction unit 117.

The exemplary embodiment illustrated in FIG. 2 is a case in which the electrode part 115 is positioned below the channel 114 when the plasma passing through the membrane 113 flows in the channel 114. The exemplary embodiment illustrated in FIG. 3 is a case in which the electrode part 115 is positioned above the channel 114.

The loading hole cover 111 is a cover having a loading hole into which the blood is loaded. The loading hole cover 111 prevents the blood from flowing to the remaining region except for the loading hole. The loading hole cover 111 blocks the channel cover 112, the membrane 113, the channel 114, or the electrode part 115 from the outside so that the plasma, which is separated from the blood introduced through the loading hole, may move in the direction of the channel.

The channel cover 112 may be attached to an upper surface of the channel 114 (see FIG. 2) or attached to a lower surface of the channel (see FIG. 3), thereby guiding the plasma so that the plasma flows to the electrode part 115. The electrode part 115 is positioned on the lower portion of the channel 114 when the channel cover 112 is positioned on the upper portion of the channel 114, and the electrode part 115 may be positioned on the lower portion of the channel 114 when the channel cover 112 is positioned on the lower portion of the channel 114.

The membrane 113 separates the blood cells from the blood (whole blood) and supplies the plasma to the channel 114. The membrane 113 will be described in detail with reference to FIG. 4.

FIG. 4 is an enlarged view of the membrane 113 according to the exemplary embodiment of the present invention.

The membrane 113 has pores having non-uniform sizes, a size of the pore at a portion of the membrane, which adjoins the channel 114, may be smaller than a size of the pore at a portion of the membrane where the whole blood is introduced. For example, a size of the pore may become smaller in a direction from the upper portion to the lower portion of the membrane 113. The pore at the upper portion of the membrane is sized to prevent the blood cell from passing through the pore, such that the blood cell having a larger size cannot pass through the membrane. Assuming that the membrane 113 has a hexahedral shape, the whole blood is loaded into an upper side of the membrane, and the plasma may flow out through five sides except for the upper side. As another exemplary embodiment, the four wall surfaces of the membrane have no pore or have small pores that cannot allow the plasma to pass therethrough so that the plasma cannot pass through the membrane. However, the size of the pore becomes smaller in the direction from the upper portion to the lower portion, such that the plasma may flow out only through the lower surface of the membrane. In this case, the pores in the four wall surfaces of the membrane may be formed to have the smallest size in the membrane 113.

As still another exemplary embodiment, referring to FIG. 2, the surface of the membrane 113, which is adjacent to the channel cover 112, may have no pore or have smallest pores in the membrane 113 so that the plasma cannot pass through the pores.

Referring to FIG. 3, the surface of the membrane 113, which is adjacent to the electrode part 115, may have no pore or have smallest pores in membrane 113 so that the plasma cannot pass through the pores.

In a case in which the membrane 113 adjoins any one of the electrode part 115 and the channel cover 112, a part of the upper portion of the membrane 113 may cover the upper portion of the electrode part 115 or the channel cover 112. In this case, there is an effect in that the plasma passing through the membrane 113 does not leak into a space between the membrane 113 and the electrode part 115 or between the membrane 113 and the channel cover 112.

In addition, as illustrated in FIG. 2, a cavity is formed in the lower portion of the surface of the membrane 113 with which the channel cover 112 comes into contact, such that the plasma passing through the membrane 113 does not flow between the channel cover 112 and the channel 114. In FIG. 3, the cavity is formed in the lower portion of the surface of the membrane 113 with which the electrode part 115 comes into contact, such that the plasma passing through the membrane 113 is prevented from leaking between the electrode part 115 and the channel 114.

The channel 114 is a passageway through which the plasma separated by the membrane 113 flows.

The plasma flowing in the channel 114 moves to the reaction unit 117 of the electrode part 115. Because the channel is opened at an end thereof, the plasma in the channel 114 may flow based on the capillary phenomenon without separate power.

The electrode part 115 includes electrodes that transmit an electrochemical signal to the signal analysis part 130, and the electrodes adjoin one surface of the channel 114 and come into contact with the plasma flowing in the channel 115.

The electrode part 115 includes the device recognition unit 116 and the reaction unit 117. When the blood analysis device according to the present invention is inserted into a slot of an external recognition device, the device recognition unit 116 enables the external recognition device to ascertain that the blood analysis device according to the present invention is connected to the slot.

The reaction unit 117 is coated with protein/nucleic acid needed in accordance with substances to be analyzed. For example, the reaction unit 117 is coated with an enzyme coating made of an oxidase-based material using glucose, such as GOx or GDH in order to analyze glucose, and coated with a related antibody or aptamer in order to analyze an antigen related to a disease.

Meanwhile, a region of the electrode part 115, except for the device recognition unit 116 and the reaction unit 117, may be coated with an insulator. The number of electrodes constituting the electrode part 115 may be 2 or 3.

The electrode part 115 may include a working electrode WE and a counter electrode CE. When the plasma flowing in the channel comes into contact with both the working electrode and the counter electrode, it can be considered that the plasma required to be analyzed sufficiently flows into the channel.

The filler 118 may connect the membrane 113 and the lower surface of the channel 114 and push up, by a predetermined height, a portion of the membrane 113 with which the filler 118 comes into contact. It is difficult for the plasma to easily pass through the membrane 113 because of surface tension, but the surface tension may be reduced as the filler 118 connects the membrane and the lower portion of the channel 114 and an end of the filler 118 pushes up the membrane 113 by a predetermined height.

FIGS. 5A to 5E are views illustrating a detailed configuration of the stationary blood loading part 100 according to the exemplary embodiment of the present invention.

Referring to FIGS. 5A to 5E, the blood loading part 100 according to the present exemplary embodiment includes a capillary part 500 and a capillary holder 510.

The capillary part 500 supplies the loaded blood to the membrane 113, and the capillary holder 510 guides the capillary part 500 to the membrane 113.

FIG. 5A illustrates a state in which the capillary part 500 is supported by the capillary holder 510 and is in contact with the membrane 113 before the blood is supplied to the capillary part 500.

In FIG. 5B, when the blood is supplied to the capillary part 500, the blood moves toward a lower side of the capillary part 500.

In FIG. 5C, when the capillary part 500 is fully filled with the blood, the blood flows out from an outlet of the capillary part 500 and begins to be absorbed into the membrane 113.

In FIG. 5D, when the blood is absorbed into the membrane 113 and thus a color is changed, the additional loading of the blood is stopped.

In FIG. 5E, when a sufficient amount of blood is absorbed into the membrane 113, the supply of blood to the membrane 113 is automatically stopped.

In FIG. 5E, the reason why the supply of blood is automatically stopped is that all of the pores in the upper portion of the membrane 113 are blocked when the time has elapsed after the blood cells are filtered out by the pores in the upper portion of the membrane 113 as illustrated in FIG. 4. Therefore, when a predetermined time has elapsed after the supply of blood to the membrane 113, the blood is not absorbed into the membrane 113. Therefore, it is possible to adjust the amount of blood to be supplied to the membrane 113 in accordance with the number, the size, or the density of the pores in the upper portion of the membrane 113.

FIGS. 6A to 6C are views illustrating a detailed configuration of a stationary blood loading part 100 according to another exemplary embodiment of the present invention.

There is a difference between the stationary blood loading parts 100 illustrated in FIGS. 5A to 5E and FIGS. 6A to 6C in that the stationary blood loading part 100 illustrated in FIGS. 5A to 5E supplies the blood to the capillary part 500 after the capillary part 500 comes into contact with the membrane 113, but the stationary blood loading part 100 illustrated in FIGS. 6A to 6C brings the membrane 113 into contact with the capillary part 500 after the capillary part 500 is filled with the blood.

In FIGS. 6A to 6C, the amount of blood loaded into the capillary part 500 is determined by calculating in advance a maximum amount of blood that may be absorbed into the membrane 113. Therefore, as illustrated in FIG. 5D, it is not necessary to stop the loading of the blood by checking the change in color of the membrane 113. The amount of blood, which may be loaded into the capillary part 500, may be adjusted in accordance with the number, the size, or the density of the pores in the upper portion of the membrane 113.

FIGS. 7A and 7B are views illustrating a detailed configuration of a rotary blood loading part 100 according to still another exemplary embodiment of the present invention.

Referring to FIGS. 7A and 7B, the blood loading part 100 according to the present exemplary embodiment includes the capillary part 500, the capillary holder 510, and the rotation part 520.

The blood loaded into the capillary part 500 is supplied to the membrane, and the capillary holder 510 guides the capillary part 500 to the membrane.

The rotation part 520 is coupled to the capillary part 500 and rotates the capillary part 500 to position the capillary part 500 on the capillary holder 510. The rotation part 520 moves the capillary part 500 in a direction of the capillary holder 510 so that the capillary part 500 passes through the loading hole and comes into contact with the membrane 113.

FIGS. 8A to 8C are views illustrating a process of supplying blood to the membrane 113 by using the rotary blood loading part 100 illustrated in FIGS. 7A and 7B.

FIG. 8A illustrates a state in which the blood is loaded into the capillary part 500 of the rotary blood loading part 100. FIG. 8B illustrates a state in which the capillary part 500 into which the blood is loaded is rotated by 90 degrees by the rotation part 520 and positioned on the upper portion of the capillary holder 510. FIG. 8C illustrates a state in which the capillary part 500 coupled to the rotation part 520 is guided to the capillary holder 510 through the loading hole.

In FIGS. 8A to 8C, the amount of blood loaded into the capillary part 500 may be determined by calculating in advance a maximum amount of blood that may be absorbed into the membrane 113.

FIGS. 9A to 9C are views illustrating a state in which the capillary holder 510 is inclined at an angle of 45 degrees with respect to the upper surface of the membrane 113.

FIG. 9A is a view illustrating a state in which the capillary part 500 is inserted into the capillary holder 510 in a direction of 45 degrees, and FIG. 9B illustrates a state in which the capillary part 500 coupled to the rotation part 520 is inserted into the capillary holder 510 after being rotated by 45 degrees. FIG. 9C is a view illustrating a state in which a bottom surface of the capillary is cut along an oblique line in order to increase a contact surface with the membrane 113 when the capillary part 500 is inserted into the capillary holder 510 in the direction of 45 degrees.

The amount of blood, which may be loaded into the capillary part 500, may be changed when a width and a length of the capillary part 500 into which the blood is loaded are changed. Therefore, it is possible to quantify the amount of blood to be loaded into the membrane 1130 by using the width and the length of the capillary part 500. Meanwhile, a material of the capillary may be glass, plastic, metal, or the like. Referring to FIGS. 8A to 8C and 9A to 9C, an angle between the capillary holder 510 and the membrane 113 may be 0 degree to 90 degrees.

FIGS. 10A and 10B are views illustrating the blood loading part 100 in which an inner portion of the capillary holder 510 is coated with a hydrophilic coating without the capillary part 500 to load blood.

Referring to FIGS. 10A and 10B, the inner portion of the capillary holder 510 is coated with a hydrophilic coating, thereby guiding, to the membrane 113, the blood loaded into the capillary holder 510.

In this case, FIG. 10A illustrates a case in which an angle between a direction of the supply of blood into the capillary holder 510 and the upper surface of the membrane is 0 degree (or 180 degrees), and FIG. 10B illustrates a case in which an angle between the direction of the supply of blood into the capillary holder 510 and the upper surface of the membrane is 90 degrees (or −90 degrees).

FIGS. 11A to 11D are views illustrating detecting electrodes DE1, DCE, WE, CE, and DE2 included in the electrode part 115 according to the exemplary embodiment of the present invention.

FIGS. 11A and 11B are a cross-sectional view and a top plan view of the blood analysis device according to the exemplary embodiment of the present invention, and FIGS. 11C and 11D are a cross-sectional view and a top plan view of a blood analysis device according to another exemplary embodiment of the present invention.

The plasma passing through the membrane 113 has a large deviation in a total amount or viscosity of the plasma in accordance with the state of the blood. Therefore, because the amount of time required to separate the plasma varies, there is a need for a detection method of checking a degree to which the plasma is loaded.

Referring to FIGS. 11A and 11B, when the plasma passing through the membrane 113 comes into contact with the first detecting electrode DE1 and the detecting counter electrode DCE, it is detected that the plasma begins to be loaded into the channel. In this case, the DE1 and the DCE may be positioned on the lower portion of the membrane 113 or positioned at an upper end of the electrode part 115.

After the plasma flows in the channel through the first detecting electrode DE1 and the detecting counter electrode DCE for a predetermined time, the plasma reaches the working electrode WE and the counter electrode CE. When the plasma reaches the working electrode and the counter electrode and comes into contact with the second detecting electrode DE2, it may be detected that the loading of the plasma into the channel is completed.

The second detecting electrode DE2, the working electrode WE, and the counter electrode CE may be positioned at one end of the channel 114 so that the plasma flowing in the channel 114 reaches the second detecting electrode DE2, the working electrode WE, and the counter electrode CE.

As another exemplary embodiment, referring to FIGS. 11C and 11D, when the plasma passing through the membrane 113 comes into contact with the first detecting electrode DE1 and the detecting counter electrode DCE, it is detected that the plasma begins to be loaded into the channel. In this case, the DE1 and the DCE may be positioned on the lower portion of the membrane 113 or positioned at an upper end of the channel cover 112.

After the plasma flows in the channel through the first detecting electrode DE1 and the detecting counter electrode DCE for a predetermined time, the plasma reaches the working electrode WE and the counter electrode CE. When the plasma reaches the working electrode and the counter electrode and comes into contact with the second detecting electrode DE2, it may be detected that the loading of the plasma into the channel is completed. The second detecting electrode DE2, the working electrode WE, and the counter electrode CE may be positioned at one end of the channel 114 so that the plasma flowing in the channel 114 reaches the second detecting electrode DE2, the working electrode WE, and the counter electrode CE.

FIGS. 12A and 12B are views illustrating a state in which a plasma transporting electrode PTE included in the plasma guide part 120 according to the exemplary embodiment of the present invention is added to the configuration illustrated in FIGS. 11A to 11D.

Referring to FIG. 12A, the plasma guide part 120 includes, below the channel cover 112, a plasma transporting electrode PTE and an insulator that adjoins the PTE. In addition, in FIG. 12A, the PTE may be disposed below the channel cover 112, or the PTE may be disposed below the channel 114.

Meanwhile, in FIG. 12B, the PTE is disposed on the upper portion of the channel cover 112, and the insulator is disposed above the PTE.

FIG. 13 is an enlarged view of part A of the PTE illustrated in FIGS. 12A and 12B.

Referring to FIG. 13, the PTE includes a plurality of electrodes disposed in parallel in the direction of transport of the plasma. It is possible to move the plasma even though the PTE includes a single electrode.

The PTE is an electrode capable of moving the plasma in an electro-wetting manner in a direction of a portion where the electrode is present.

The electro-wetting refers to a phenomenon in which when an electrode and a polar liquid are positioned with an insulator disposed therebetween and then voltage is applied to the electrode, surface tension of the polar liquid is changed. By using the electro-wetting, the polar liquid moves along the electrode to which the voltage is applied.

Referring back to FIGS. 12A and 12B, in a case in which the DE2 does not generate a signal when a predetermined time has elapsed after the plasma reaches the DE1 and the DE1 generates a signal, the PTE may be used to forcibly move the plasma in the channel 114.

As illustrated in FIG. 13, assuming that numbers 1, 2, 3 . . . are assigned to the electrodes from left to right, the electrodes for applying voltage may be turned on/off in the order of 1, 2→2, 3→3, 4, thereby moving, to the electrodes, the plasma flowing into channel disposed below the insulator.

FIGS. 14A and 14B are views illustrating a state in which a plasma transporting electrode PTE included in a plasma guide part 120 according to another exemplary embodiment of the present invention is added to the configuration illustrated FIGS. 11A to 11D.

FIGS. 12A and 12B illustrate that the PTE is vertically disposed above (FIG. 12B) or below (FIG. 12A) the channel cover 112, and FIGS. 14A and 14B illustrates that the PTE is horizontally disposed on the wall surface of the channel 114. In this case, the insulator may be positioned between the channel 114 and the PTE.

When the PTE is horizontally disposed on the wall surface of the channel 114, a size is decreased as much as a vertical space occupied by the PTE in comparison with the vertical arrangement of the PTE illustrated in FIGS. 12A and 12B. Further, since the PTE is disposed on the wall surface of the channel 114, an influence of an electric field on other electrodes may be reduced in comparison with the layered structure illustrated in FIGS. 12A and 12B.

FIG. 15 is a flowchart of a blood analysis method to an exemplary embodiment of the present invention.

Referring to FIG. 15, a blood analysis method according to the present exemplary embodiment includes steps performed in a time series by the blood analysis device illustrated in FIGS. 1 to 14B. Therefore, the contents described above in respect to the blood analysis device illustrated in FIGS. 1 to 14B are also applied to the blood analysis method to the present exemplary embodiment even though the contents will be omitted below.

In step 1500, the blood analysis device determines whether the internal electrodes included in the blood analysis device are positioned at predetermined positions. The internal electrodes include the first detecting electrode DE1, the detecting counter electrode DCE, the second detecting electrode DE2, the working electrode WE, the counter electrode CE, and the plasma transporting electrode PTE. In particular, the device recognition unit 116 may check whether the blood analysis device according to the present invention is connected to the slot of the external recognition device when the blood analysis device according to the present invention is inserted into the slot of the external recognition device, thereby checking whether the working electrode WE and the counter electrode CE are positioned at the predetermined positions.

While step 1510 is performed when it is determined in step 1500 that the internal electrodes are not positioned at the predetermined positions, step 1520 is performed when it is determined that the internal electrodes are positioned at the predetermined positions.

In step 1510, the indication showing that the internal electrodes need to be inserted again is displayed on a display device of the blood analysis device. When the internal electrodes are inserted again, whether all of the internal electrodes are positioned at the predetermined positions is determined again in step 1500.

In step 1520, the blood analysis device determines whether the first detecting electrode DE1 and the detecting counter electrode DCE are electrically connected after the blood is loaded. When the first detecting electrode DE1 and the detecting counter electrode DCE are electrically connected, whether the plasma reaches the first detecting electrode DE1 is detected, which means that the blood is sufficiently supplied to the membrane.

Meanwhile, when the first detecting electrode DE1 and the detecting counter electrode DCE are not electrically connected, step 1530 of displaying the indication showing that the blood needs to be additionally loaded is performed. When the first detecting electrode DE1 and the detecting counter electrode DCE are electrically connected, step 1540 is performed.

In step 1540, the blood analysis device displays, on the display device, a message showing that the loading of the plasma is in progress for a predetermined time for which the plasma passing through the membrane flows in the channel and reaches the second detecting electrode DE2.

In step 1550, the blood analysis device is on standby for the predetermined time. The predetermined time varies depending on a movement speed of the plasma and a length of the channel.

In step 1560, the blood analysis device determines whether the second detecting electrode DE2 and the DCE are electrically connected after the predetermined time.

When the second detecting electrode DE2 and the DCE are electrically connected, it is detected that the plasma reaches the second detecting electrode when a predetermined time has elapsed after the plasma reaches the first detecting electrode DE1, which means that the plasma flowing in the channel also reaches the working electrode WE positioned at one end of the channel so that an electrochemical signal of the plasma may be measured.

In step 1560, when the second detecting electrode DE2 and the DCE are electrically connected after the predetermined time, step 1590 may be performed without performing step 1580.

However, when the second detecting electrode DE2 and the DCE are not electrically connected even when the predetermined time has elapsed, step 1570 is performed to operate the plasma transporting electrode to move the plasma. The plasma transporting electrode may be positioned at any one of the upper, lower, left, and right sides of the channel. Referring back to FIGS. 12A and 12B, the plasma transporting electrodes are positioned at the upper and lower sides of the channel 114. Further, referring to FIGS. 14A and 14B, the plasma transporting electrodes are positioned at the left and right sides of the channel 114.

In step 1580, the blood analysis device stops the operation of the plasma transporting electrode that has operated in step 1570.

In step 1590, the blood analysis device measures an electrochemical signal of the plasma that has reached the working electrode WE.

While the present invention has been described above with reference to particular contents such as specific constituent elements, the limited exemplary embodiments, and the drawings, but the exemplary embodiments are provided merely for the purpose of helping general understand of the present invention, and the present invention is not limited to the exemplary embodiment, and may be variously modified and altered from the disclosure by those skilled in the art to which the present invention pertains.

Accordingly, the spirit of the present invention should not be limited to the described exemplary embodiment, and all of the equivalents or equivalent modifications of the claims as well as the appended claims belong to the scope of the spirit of the present invention.

The invention claimed is:

1. A blood analysis device comprising:
 a membrane configured to separate plasma from blood;
 a channel into which the plasma separated by the membrane is introduced;
 an electrode part comprising electrodes configured to adjoin a lower portion of the channel and come into contact with the plasma flowing in the channel; and
 a channel cover configured to cover a part of an upper portion of the channel,
 wherein the membrane has a distal end portion that is placed above a part of the channel cover.

2. The blood analysis device of claim 1, further comprising:
 a cavity that is located in a space encompassed by a portion of a lower surface of the membrane, a portion of an upper surface of the channel, and a portion of a side surface of the channel cover,
 wherein the portion of the lower surface of the membrane is not placed above the part of the channel cover.

3. The blood analysis device of claim 1, wherein the membrane has pores having non-uniform sizes, and a surface of the membrane, which is adjacent to the channel cover, has no pore or smallest pores in the membrane.

4. The blood analysis device of claim 1, further comprising:
 a pillar located in the channel,
 wherein an upper end of the pillar contacts a part of a lower surface of the membrane, and a lower end of the pillar contacts a part of a lower surface of the channel, and wherein a part of the lower surface of the membrane is lifted above the other part of the lower surface of the membrane due to a height of the pillar.

5. The blood analysis device of claim 1, wherein a first detecting electrode with which the plasma comes into contact is disposed on an upper portion or a lower portion of a contact surface between the membrane and the channel.

6. The blood analysis device of claim 5, further comprising:
a plasma transporting electrode and an insulator between the channel cover and the channel,
wherein when the plasma does not reach a second detecting electrode when a predetermined time has elapsed after the plasma comes into contact with the first detecting electrode, a polarity of the plasma transporting electrode is changed to move the plasma in the channel.

7. The blood analysis device of claim 5, further comprising:
a plasma transporting electrode on an upper portion or a lower portion of a contact surface between the channel and the electrode part,
wherein when the plasma does not reach a second detecting electrode when a predetermined time has elapsed after the plasma comes into contact with the first detecting electrode, a polarity of the plasma transporting electrode is changed to move the plasma in the channel.

8. The blood analysis device of claim 5, further comprising:
a plasma transporting electrode on a left or right surface of the channel,
wherein a polarity of the plasma transporting electrode is changed to move the plasma in the channel.

9. A blood analysis device comprising:
a membrane configured to separate plasma from blood;
a channel into which the plasma separated by the membrane is introduced;
an electrode part comprising electrodes configured to adjoin a part of an upper portion of the channel and come into contact with the plasma flowing in the channel; and
a channel cover configured to cover a lower portion of the channel,
wherein the membrane has a distal end portion that is placed above a part of the electrode part.

10. The blood analysis device of claim 9, wherein a cavity that is located in a space encompassed by a portion of a lower surface of the membrane, a portion of an upper surface of the channel, and a portion of a side surface of the electrode part,
wherein the portion of the lower surface of the membrane is not placed above the part of the electrode part.

11. The blood analysis device of claim 9, wherein the membrane has pores having non-uniform sizes, and a surface of the membrane, which is adjacent to the electrode part, has no pore or smallest pores in the membrane.

12. The blood analysis device of claim 9, further comprising:
a pillar located in the channel,
wherein an upper end of the pillar contacts a part of a lower surface of the membrane, and a lower end of the pillar contacts a part of a lower surface of the channel, and
wherein a part of the lower surface of the membrane is lifted above the other part of the lower surface of the membrane due to a height of the pillar.

13. The blood analysis device of claim 9, wherein a first detecting electrode with which the plasma comes into contact is disposed on an upper portion or a lower portion of a contact surface between the membrane and the channel.

14. The blood analysis device of claim 13, further comprising:
a plasma transporting electrode and an insulator between the channel and the channel cover,
wherein when the plasma does not reach a second detecting electrode after a predetermined time has elapsed after the plasma comes into contact with the first detecting electrode, a polarity of the plasma transporting electrode is changed to move the plasma in the channel.

15. The blood analysis device of claim 13, further comprising:
a plasma transporting electrode on a left or right surface of the channel,
wherein a polarity of the plasma transporting electrode is changed to move the plasma in the channel.

16. The blood analysis device of claim 1,
wherein the electrodes comprises a working electrode and a counter electrode, which are spaced apart, and wherein each of the working electrode and the counter electrode is attached to one surface of an enzyme coating, which has another surface located inside the channel.

17. The blood analysis device of claim 9,
wherein the electrodes comprises a working electrode and a counter electrode, which are spaced apart, and wherein each of the working electrode and the counter electrode is attached to one surface of an enzyme coating, which has another surface located inside the channel.

18. The blood analysis device of claim 1, wherein the distal end portion of the membrane is placed directly above the part of the channel cover.

19. The blood analysis device of claim 9, wherein the distal end portion of the membrane is placed directly above the part of the electrode part.

* * * * *